United States Patent
Holms et al.

(10) Patent No.: US 9,682,140 B2
(45) Date of Patent: Jun. 20, 2017

(54) EZRIN-DERIVED PEPTIDES AND PHARMACEUTICAL COMPOSITIONS THEREOF

(71) Applicant: Nearmedic International Limited, Nicosia (CY)

(72) Inventors: Rupert Holms, London (GB); Ravshan Ataullakhanov, Moscow (RU); Rustam Ataullakhanov, Moscow (RU); Khachik Sayadyan, Moscow (RU)

(73) Assignee: NEARMEDIC INTERNATIONAL LIMITED (CY)

( * ) Notice: Subject to any disclaimer, the term of this patent is extended or adjusted under 35 U.S.C. 154(b) by 0 days.

(21) Appl. No.: 15/170,362

(22) Filed: Jun. 1, 2016

(65) Prior Publication Data
US 2016/0346383 A1   Dec. 1, 2016

(51) Int. Cl.
*A61K 38/00* (2006.01)
*A61K 39/39* (2006.01)
*C07K 7/08* (2006.01)
*C07K 14/47* (2006.01)
*A61K 39/00* (2006.01)

(52) U.S. Cl.
CPC ............. *A61K 39/39* (2013.01); *C07K 7/08* (2013.01); *C07K 14/4713* (2013.01); *A61K 38/00* (2013.01); *A61K 2039/55516* (2013.01); *A61K 2039/57* (2013.01)

(58) Field of Classification Search
None
See application file for complete search history.

(56) References Cited

FOREIGN PATENT DOCUMENTS

WO   01/25275 A1   4/2001

OTHER PUBLICATIONS

McNab, et al, Type I interferons in infectious disease, Nature Reviews (Immunology) vol. 15, 2015, p. 87-103.*
MedicineNet.com 2016, pp. 1-3.*
Salamov et al., (2007) "Treatment of Hepatitis C Virus Infection with Human Ezrin Peptide One (HEP1) in HIV Infected Patients", Arzneimittei-Forsclumg (Drug Research); vol. 57, No. 7; pp. 497-504.

* cited by examiner

Primary Examiner — Thomas S Heard
(74) Attorney, Agent, or Firm — Riverside Law LLP

(57) ABSTRACT

The present invention relates to the field of medicine, specifically, to the field of chemical and pharmaceutical industry and concerns ezrin-derived peptides, in particular, a peptide comprising an amino acid sequence of general formula (I) $X_1$ EKKRRETVERE $X_2X_3$, wherein each X represents a non-polar amino acid residue. The use of the peptides as immunostimulatory agents, and more specifically, for use in treating and preventing antiviral, antibacterial and antifungal infections, and treatment of diseases of the GI tract, in particular ulcerative disorders of the GI tract. The present invention also relates to pharmaceutical compositions comprising the peptides. Further, the invention relates to methods of treatment of infection and ulcerative diseases of the GI tract comprising administering the peptides to patients in need thereof.

10 Claims, 6 Drawing Sheets

EZRIN-DERIVED PEPTIDES AND PHARMACEUTICAL COMPOSITIONS THEREOF

Figure 1:
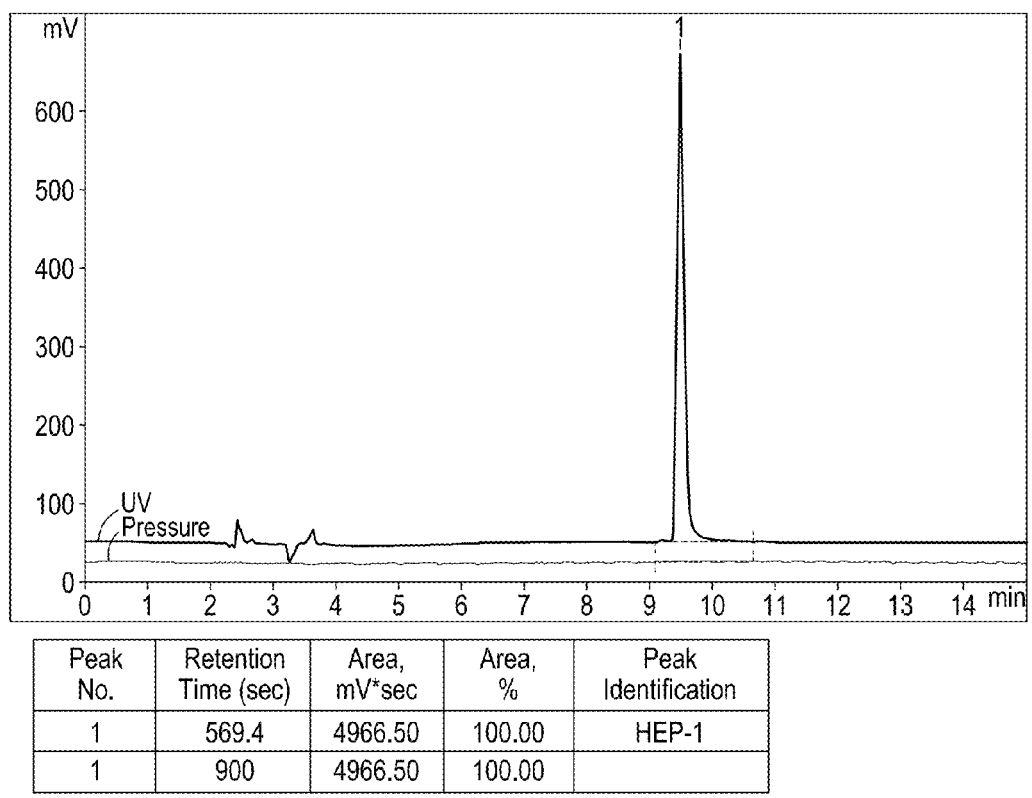

The present invention relates to the field of medicine, specifically, to the field of chemical and pharmaceutical industry and concerns ezrin-derived peptides, in particular, a peptide comprising an amino acid sequence of general formula (I) $X_1$ EKKRRETVERE $X_2X_3$, wherein each X represents a non-polar amino acid residue. The use of the peptides as immunostimulatory agents, and more specifically, for use in treating and preventing antiviral, antibacterial and antifungal infections, and treatment of diseases of the GI tract, in particular ulcerative disorders of the GI tract. The present invention also relates to pharmaceutical compositions comprising the peptides. Further, the invention relates to methods of treatment of infection and ulcerative diseases of the GI tract comprising administering the peptides to patients in need thereof.

Ezrin protein, also known as cytovillin or villin-2, is a protein encoded in humans by the EZR gene. Peptides derived from ezrin protein, having biological activity, are well-known. The closest analogue to the peptide of the invention is a pharmaceutical tetradecapeptide NH$_2$ Thr-Glu-Lys-Lys-Arg-Arg-Glu-Thr-Val-Glu-Arg-Glu-Lys-Glu_COOH, comprising 14 amino acid residues, which is known as HEP-1 peptide or human ezrin peptide one (sequence ID No. 2: TEKKRRETVEREKE) and which was developed for the treatment of HIV-infection [R. D. Holms, AIDS prophylactics. PCT/GB95/001285, Jun. 2, 1995, WO 95/33768] and, further, for the treatment of a wide range of bacterial, fungal, and viral infections.

Lyophilized pharmaceutical product GEPON® (marketing authorization number: P N000015/01-010911), comprising about 96% of HEP-1 peptide, is widely used for medical proposes in the Russian Federation (Kladova, O. V., Kharlamova, F. S., Shcherbakova, A. A., Legkova, T. P, Feldfix, L. I., Znamenskaya, A. A., Ovchinnikova, G. S., Uchaikin, V. F. *The first experience of Hepon intranasal application in children with respiratory infections.//Pediatrics,* 2002, No. 2, pp. 86-88), (Polyakova T. O., Magomedov, M. M, Artemyev, M. E., Surikov, E. V., Palchun, V. T. *A new approach in the treatment of chronic diseases of the pharynx//Attending Doctor,* 2002, No. 4, pp. 64-65), (Novokshonov, A. A., Uchaikin, V. F., Sokolova, N. V., Tikhonova, O. N., Portnykh, O. Yu. *Biocenosis-protecting therapy of intestinal infections in children.//Russian Medical Journal, special supplement "Diseases of the Digestive System",* 2004, volume 6, No. 1), (Parfenov, A. I. *The activator of the local immunity Hepon in the complex treatment of dysbiotic disorders of the intestine.//Experimental and Clinical Gastroenterology,* 2003, No. 3, pp. 66-69). (Tishchenko, A. L. *A new approach in the treatment of recurrent urogenital candidiasis.//Attending Doctor,* 2002, No. 3, pp. 46-47), (Telunts, A. V. *Treatment of candidiasis in infants.//Questions of Gynecology, Obstetrics, and Perinatology,* 2004, vol. 3, No. 4, pp. 89-90), (Ataullakhanov, R. I., Holms, R. D., Katlinsky, A. V., Pichugin A. V., Papuashvili, M. N., Shishkova, N. M. *Treatment with Hepon immunomodulator increases the efficacy of the immune control of opportunistic infections in HIV-infected patients.//Allergy, Asthma, and Clinical Immunology,* 2002, No. 10, pp. 3-11), (Cherednichenko, T. V., Uchaikin, V. F., Chaplygina, G. V., Kurbanova, G. M. *A new efficient treatment of viral hepatitis.// Attending Doctor,* 2003, No. 3, pp. 82-83), (Gorbarets, I. P., Voronkova, N. V., Lopatina, T. V., Ivanovskaya, V. N., Braginsky, D. M., Blokhina, N. P., Malyshev, N. A. *The combined use of Hepon drug product and recombinant interferon-alpha in the patients with chronic hepatitis C increases the efficiency of antiviral treatment and reduces side effects of the therapy.//Hepatology,* 2003, No. 4, pp. 23-28), (Lazebnik, L. B., Zvenigorodskaya, L. A., Firsakova, V. Yu., Pichugin, A. V., Ataullakhanov, R. I. *The application of Hepon immunomodulator in the treatment of erosive ulcerous lesions of gastroduodenal zone.//Experimental and Clinical Gastroenterology,* 2003, No. 3, pp. 17-20), (Malakhova, N. S., Pichugin, A. V., Khalif, I. L., Ataullakhanov, R. I. *The application of Hepon immunomodulator for the treatment of nonspecific ulcerative colitis.//Farmateka,* 2005, No. 6 [101], pp. 105-108), Dudchenko, M. A., Lysenko, B. F., Chelishvili, A. L., Katlinsky, A. V., Ataullakhanov, R. R. *Complex treatment of trophic ulcers.//Attending Doctor,* 2002, No. 10, pp. 72-75), (Bardychev, M. S. *Treatment of local radiation injuries with the activator of local immunity.//Russian Medical Journal,* 2003, volume 11, No. 11 (183), pp. 646-647), Salamov G., R. Holms, W. Bessler, R. Ataullakhanov. Treatment of hepatitis C virus infection with human ezrin peptide one (HEP1) in HIV infected patients.//Arzneimittel-Forschung (Drug Research) 2007; 57(7): 497-504].

HEP-1 has anti-viral hepatitis C biological activity and can be used for the treatment of the patients with hepatitis C [R. D. Holms, R. I. Ataullakhanov. HCV combination therapy. PCT/GB2004/000330, Jan. 27, 2004, WO 2004067024 A2].

HEP-1 has antiulcer biological activity and can be used for the treatment of ulcer diseases of the gastrointestinal tract [R. D. Holms, R. I. Ataullakhanov. The use of peptides in anti-ulcer therapy. PCT/GB2006/004390, Nov. 23, 2006, WO/2007/060440].

The present inventors have developed a novel peptide which was prepared synthetically and which has high immunostimulatory activity. As biological tests have shown, the peptide of the invention as described and pharmaceutical compositions thereof have high immunostimulatory activity, exceeding the activity of HEP-1 peptide, which is the main component of GEPON® drug product.

In a first aspect of the invention, there is provided a peptide comprising an amino acid sequence of general formula (I) $X_1$EKKRRETVEREX$_2$X$_3$, wherein each of $X_1$, $X_2$ and $X_3$ represent a non-polar amino acid residue (SEQ ID No: 5).

Non-polar amino acid residues can be independently selected from the group consisting of glycine, alanine, valine, leucine, methionine, isoleucine, proline, phenylalanine and tryptophan, and/or combinations thereof.

In some embodiments, $X_1$, $X_2$ and/or $X_3$ can be independently selected from non-polar amino acids having small R groups, in particular glycine, alanine and/or valine, and/or combinations thereof. Thus, in some embodiments of the invention, each of $X_1$, $X_2$ and $X_3$ are independently selected from the group consisting of glycine, alanine and valine.

In some embodiments, $X_1$, $X_2$ and/or $X_3$ can all be the same amino acid. In a preferred embodiment, at least one of $X_1$, $X_2$ and $X_3$ is glycine. In a more preferred embodiment, at least 2 of $X_1$, $X_2$ and $X_3$ is glycine. In the most preferred embodiment, each of $X_1$, $X_2$ and $X_3$ is glycine. In one embodiment, the peptide comprises an amino acid sequence of general formula (I) $X_1$ EKKRRETVERE $X_2X_3$, wherein each of $X_1$, $X_2$ and $X_3$ are non-polar, and further wherein at least one, or at least two, of $X_1$, $X_2$ and $X_3$ are glycine. In a preferred embodiment, the peptide has the sequence GEKKRRETVEREGG.

In the present disclosure, the one letter codes have been used to designate the various amino acids. Using the three letter and one letter codes the amino acids may also be referred to as follows: glycine (G or Gly), alanine (A or Ala), valine (V or Val), leucine (L or Leu), isoleucine (I or Ile), proline (P or Pro), phenylalanine (F or Phe), tyrosine (Y or Tyr), tryptophan (W or Trp), lysine (K or Lys), arginine (R or Arg), histidine (H or His), aspartic acid (D or Asp), glutamic acid (E or Glu), asparagine (N or Asn), glutamine (Q or Gln), cysteine (C or Cys), methionine (M or Met), serine (S or Ser) and threonine (T or Thr). Where a residue may be aspartic acid or asparagine, the symbols Asx or B may be used. Where a residue may be glutamic acid or glutamine, the symbols Glx or Z may be used. References to aspartic acid include aspartate, and glutamic acid include glutamate, unless the context specifies otherwise.

The term peptide may include compositions comprising the amino acid sequences disclosed herein. For example, peptides may be modified (for example at the C or N terminals) to protect them from degradation or to increase their bioavailability and/or biocompatibility, as deemed suitable or required by the skilled person. It is noted that features relating to "peptide of the invention" apply equally to the amino acid sequence specified in the general formulae.

The peptide of the invention may be of any length provided the amino acid sequence comprises the general formula (I) $X_1EKKRRETVEREX_2X_3$, wherein each X represents a non-polar amino acid residue, as described herein.

In some embodiments, the peptide is 14 to 25 residues in length, for example 14 to 20 residues in length, or 14 to 18 residues in length and comprises the amino acid sequence of general formula (I) (or further defined embodiments thereof). In some embodiments, the peptide is 14, 15, 16, 17, 18, 19, 20, 21, 22, 23, 24 or 25 residues in length and comprises amino acid sequence of general formula (I) (or further defined embodiments thereof). In further embodiments, the peptide is 14 to 25 residues in length, for example 14 to 20 residues in length, or 14 to 18 residues in length and comprises the sequence of SEQ ID No: 1 (GEKKRRETVEREGG). In some embodiments, the peptide is 14, 15, 16, 17, 18, 19, 20, 21, 22, 23, 24 or 25 residues in length and comprises the sequence of SEQ ID No: 1 (GEKKRRETVEREGG). In one embodiment, the peptide is between 14 and 18 residues in length and comprises an amino acid sequence of general formula (I) $X_1$ EKKRRETVERE $X_2X_3$, wherein each of $X_1$, $X_2$ and $X_3$ are non-polar, and further wherein at least two of $X_1$, $X_2$ and $X_3$ are glycine. In preferred embodiments, the peptide of the invention is at least 14 amino acids in length and comprises SEQ ID No: 1 (GEKKRRETVEREGG).

Preferably, the peptide of the invention is 14 amino acid residues in length. In the most preferred embodiment of the invention, the peptide has the sequence of NH2_Gly-Glu-Lys-Lys-Arg-Arg-Glu-Thr-Val-Glu-Arg-Glu-Gly-Gly_ COOH (sequence ID No. 1: GEKKRRETVEREGG) (herein referred to as HP-V2).

The objective of the present invention is the extension of the range of peptide compounds having enhanced immunostimulatory activity. Moreover, the objective of the present invention is the preparation of a pharmaceutical composition with the highest immunostimulatory activity and with a wide range of action on the basis of the claimed peptide and known Ezrin peptides. Generally, the peptides of the invention have a higher immunostimulatory profile and/or a higher antiviral activity when compared to peptides comprising or consisting of SEQ ID No: 2. Immunostimulation and antiviral activity may be measured by any method known to a skilled person. For example, the immunological activity of the peptide can be assessed according to the effect on the synthesis of cytokine mRNA in J-96 cells (for example: IFN-α, IL-1β and IL-6). Antiviral activity can be measured according to the cytotoxic effect on Encephalomyocarditis Virus (ECM) and/or according to the IC50 for the peptide in inhibiting EMC virus replication. Other methods would be apparent to the skilled person.

The desired objective can be achieved with the proposed novel peptide comprising the sequence of formula (I), and derivatives thereof as discussed herein, and more particularly the sequence of SEQ ID No. 1: GEKKRRETVEREGG. These peptides of the invention are prepared synthetically and have high immunostimulatory activity. A search of the peptide sequences in the database http://research.bloinformatics.udcl.edu/peptidematch/index.jsp and a search of the protein sequences in the database http://www.uniprot.org-blast/ has confirmed the novelty of the peptide (HP-V2), comprising 14 amino acid residues (sequence ID No. 1: GEKKRRETVEREGG).

As biological tests have shown, the peptide of the invention and pharmaceutical compositions thereof have high immunostimulatory activity, exceeding the activity of HEP-1 peptide, which is the main component of GEPON® drug product.

Known ezrin peptide HEP-1 (sequence ID No. 2: TEKKRRETVEREKE), and two smaller peptides: HP1-5 peptide of the formula $NH_2$ Thr-Glu-Lys-Lys-Arg COOH (sequence ID No. 3: TEKKR) hereinafter defined as HP1-5, and HP6-14 peptide of the formula $NH_2$ Arg-Glu-Thr-Val-Glu-Arg-Glu-Lys-Glu_COOH (sequence ID No. 4: RETVEREKE) hereinafter defined as HP6-14, were used for the preparation of pharmaceutical compositions with the peptide of the invention. The latter two peptides are cleavage products of HEP1 peptide (sequence ID No. 2: TEKKRRETVEREKE) and have sequences, which are identical to those described previously [R. D. Holms. Regulatory/unfolding peptides of ezrin. PCT/GB00/03566, Sep. 15, 2000, WO 01/025275]. HP1-5 peptide and HP6-14 peptide are two satellite peptides, which were found in GEPON® drug product as impurities.

In some embodiments, the peptide of the invention can be combined with HEP-1 (sequence ID No. 2: TEKKRRETVEREKE), or with HP1-5 peptide of the formula $NH_2$ Thr-Glu-Lys-Lys-Arg_COOH (sequence ID No. 3: TEKKR) hereafter defined as HP1-5, or with HP6-14 peptide of the formula $NH_2$ Arg-Glu-Thr-Val-Glu-Arg-Glu-Lys-Glu_ COOH (sequence ID No. 4: RETVEREKE) hereafter defined as HP6-14.

Peptides of the invention and combinations of peptides as described herein may be useful in medicine, for example for use in the treatment and prevention of viral, bacterial and fungal infections, as well as for the treatment of ulcer diseases of mucous membranes and soft tissues.

In a second aspect of the invention, there is provided a peptide of the invention (such as a peptide of general formula (I), in particular a peptide comprising the amino acid sequence of SEQ ID No: 1), for use in medicine. Particular medical uses include the treatment or prevention of infection. The infection can be a viral, bacterial or fungal infection. Further embodiments of the invention include treatment or prevention of ulceration of the mucous membranes of the gut, such as ulcers of the stomach, large intestine, duodenum or small intestine, and the treatment or prevention of inflammatory bowel diseases, including diseases and/or disorders related to ulcers of the stomach, large intestine, duodenum or small intestine, and irritable bowel syndrome (IBS). The peptides of the invention are also provided for use in the treatment or prevention of ulcerative colitis and Crohn's disease. In preferred embodiments, the peptides of the invention are provided for use in the treatment or prevention of the lower gut inflammation and/or ulceration.

There is also provided a peptide of the invention (such as a peptide of general formula (I), in particular a peptide comprising the amino acid sequence of SEQ ID No: 1), for use in stimulating an immune response in a subject. In some embodiments of the invention, the peptides can be used to stimulate endogenous production of interferon in a subject. The peptides may also be used to stimulate activation of MAPK/ERK signaling pathway.

In some embodiments of the invention, the peptide of the invention can be combined with HEP-1 (sequence ID No. 2: TEKKRRETVEREKE), or with HP1-5 peptide of the formula $NH_2$ Thr-Glu-Lys-Lys-Arg COOH (sequence ID No. 3: TEKKR) hereinafter defined as HP1-5, or with HP6-14 peptide of the formula $NH_2$ Arg-Glu-Thr-Val-Glu-Arg-Glu-Lys-Glu_COOH (sequence ID No. 4: RETVEREKE) hereinafter defined as HP6-14. For example, a peptide of general formula (I), in particular a peptide comprising the amino acid sequence of SEQ ID No: 1, can be combined with one or more of SEQ ID No: 2, 3 or 4. Such combinations are useful in the medical aspects of the invention, including treatment or prevention of infection. The infection can be a viral, bacterial or fungal infection. The combinations of peptides are also useful in the treatment or prevention of ulceration of the mucous membranes of the gut such as ulcers of the stomach, large intestine, duodenum or small intestine, and the treatment or prevention of inflammatory bowel diseases, including diseases and/or disorders related to ulcers of the stomach, large intestine, duodenum or small intestine, and irritable bowel syndrome (IBS). The peptides of the invention are also provided for use in the treatment or prevention of ulcerative colitis and Crohn's disease. In preferred embodiments, the peptide combinations of the invention are provided for use in the treatment or prevention of the lower gut inflammation and/or ulceration.

Embodiments of the invention further extend to methods of treating or preventing infections, ulcers of the stomach, large intestine, duodenum or small intestine, diseases and/or disorders related to ulcers of the stomach, large intestine, duodenum or small intestine, irritable bowel syndrome (IBS), ulcerative colitis and Crohn's disease comprising administering the peptide of the invention (such as a peptide of general formula (I), in particular a peptide comprising the amino acid sequence of SEQ ID No: 1) to a patient in need thereof. The infection may be a viral, bacterial or fungal infection. The peptides of the invention are administered in a therapeutically effective amount and may be administered with one or more other pharmaceutically active compounds. In particular, the peptides of the invention may be administered in combination with one or more of the peptides of SEQ ID No: 2, 3 and/or 4.

Thus there is also provided the combination of a peptide of the invention (such as a peptide of general formula (I), in particular a peptide comprising an amino acid sequence of SEQ ID No: 1) and a peptide comprising the amino acid sequence of SEQ ID No: 2, 3, or 4, for use in medicine. Such medical uses include treating or preventing infections (such as viral, bacterial or fungal infections), ulceration of the mucous membranes of the gut (such as stomach ulcers, large intestine ulcers, duodenal ulcers and small intestine ulcers), or inflammatory bowel disease or a disease or disorder associated with inflammatory bowel disease (such as IBS, ulcerative colitis or Crohn's disease). In preferred embodiments, the peptides of the invention are provided for use in the treatment or prevention of the lower gut inflammation and/or ulceration. Such medical uses also include stimulating an immune response in a subject.

In preferred embodiments, when the peptides of the invention are used in combination with HEP-1, HP1-5 or HP6-14, the additional peptide consists of the amino acid sequence of SEQ ID No: 2, 3, or 4.

There is also provided a method of stimulating an immune response in a subject, comprising administering a therapeutically effective amount of a peptide of the invention (such as a peptide of general formula (I), in particular a peptide comprising the amino acid sequence of SEQ ID No: 1) to a patient in need thereof.

In a third aspect of the invention, there is provided a pharmaceutical composition comprising the peptide of the invention and a pharmaceutically acceptable carrier or filler. In some embodiments of the invention, the pharmaceutical composition may further comprise an additional pharmaceutically active compound. In particular, the pharmaceutical composition may further comprise HEP-1 (sequence ID No. 2: TEKKRRETVEREKE), HP1-5 (sequence ID No. 3: TEKKR), or HP6-14 (sequence ID No. 4: RETVEREKE).

Accordingly, in one embodiment, the invention provides a pharmaceutical composition comprising a peptide of between 14 and 18 residues in length, the peptide comprising an amino acid sequence having the sequence $X_1$ EKKRRETVERE $X_2X_3$, wherein each of $X_1$, $X_2$ and $X_3$ are non-polar, and further wherein at least two of $X_1$, $X_2$ and $X_3$ are glycine, and a pharmaceutically acceptable carrier or filler.

Pharmaceutical compositions of the invention may comprise other pharmaceutically active substances, such as anti-viral, anti-bacterial, anti-fungal, analgesic and/or anti-inflammatory substances. The pharmaceutical composition may be formulated using any convenient adjuvant and/or physiologically acceptable diluents.

Fillers, carriers, preservatives, and stabilizers, which are usually used by persons skilled in drug delivery technology, may be used as an acceptable carrier or filler for preparation of the provided pharmaceutical compositions. For injections, distilled water or physiologic saline are predominantly used.

The pharmaceutical composition may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by admixing the active ingredient with the carrier (s) or excipient(s) under sterile conditions. In particular embodiments, the pharmaceutical composition of the invention comprising the peptides of the invention is in the form of a tablet for oral administration, such as a glucose tablet. In some embodiments, the table is dissolvable.

Pharmaceutical compositions adapted for oral administration may be presented as discrete units such as capsules or tablets; as powders or granules; as solutions, syrups or suspensions (in aqueous or non-aqueous liquids; or as edible foams or whips; or as emulsions). In preferred embodiments, the pharmaceutical composition of the invention comprising the peptides of the invention is in the form of a tablet for oral administration, such as a glucose table. In some embodiments, the tablet is dissolvable.

In some embodiments of the invention, the peptides are provided in the form of lyophilised powder or granules.

Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc.

For the preparation of solutions and syrups, excipients which may be used include for example water, polyols and sugars. For the preparation of suspensions oils (e.g. vegetable oils) may be used to provide oil-in-water or water in oil suspensions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research*, 3 (6), page 318 (1986).

Pharmaceutical compositions adapted for topical administration may be formulated as ointments, creams, suspensions, lotions, powders, solutions, pastes, gels, sprays, aerosols or oils. For infections of the eye or other external tissues, for example mouth and skin, the compositions are suitably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes.

Pharmaceutical compositions adapted for rectal administration may be presented as suppositories or enemas.

Pharmaceutical compositions adapted for nasal administration wherein the carrier is a solid include a coarse powder having a particle size for example in the range 20 to 500 microns. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurised aerosols, nebulizers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

The pharmaceutical compositions may contain preserving agents, solubilising agents, stabilising agents, wetting agents, emulsifiers, sweeteners, colourants, odourants, salts (substances of the present invention may themselves be provided in the form of a pharmaceutically acceptable salt), buffers, coating agents or antioxidants. They may also contain therapeutically active agents in addition to the substance of the present invention.

Dosages of the pharmaceutical compositions of the present invention can vary between wide limits, depending upon the disease or disorder to be treated, the age and condition of the individual to be treated, etc. and a physician will ultimately determine appropriate dosages to be used.

Such compositions may be formulated for human or for veterinary medicine. The present application should be interpreted as applying equally to humans as well as to animals, unless the context clearly implies otherwise.

In one embodiment, the invention provides a pharmaceutical composition in the form of a tablet for oral administration, in particular a glucose tablet, comprising a peptide of between 14 and 18 residues in length, the peptide comprising an amino acid sequence having the sequence $X_1$, EKKRRETVERE $X_2X_3$, wherein each of $X_1$, $X_2$ and $X_3$ are non-polar, and further wherein at least two of $X_1$, $X_2$ and $X_3$ are glycine, and a pharmaceutically acceptable carrier or filler. In a more preferred embodiment, the peptide has the sequence GEKKRRETVEREGG.

The invention extends to methods of manufacture of suitable pharmaceutical compositions, as well as the use of a peptide of the present invention in the manufacture of a medicament for use in medicine, for use in any of the uses specified herein.

In a further aspect of the invention, there is provided a nucleic acid sequence encoding a peptide of the invention, in particular a peptide of general formula I, such as a peptide comprising the amino acid sequence of SEQ ID No: 1 or SEQ ID No: 5.

The nucleic acid may be DNA, cDNA or RNA such as mRNA obtained by cloning or produced by chemical synthesis. The DNA may be single or double stranded. Single stranded DNA may be the coding sense strand, or it may be the non-coding or anti-sense strand.

In a still further aspect of the invention there is provided a vector comprising a nucleic acid of the invention. In yet a further aspect of the invention there is provided a host cell comprising the vector of the present invention. Methods of manufacture or obtaining of such nucleic acids, vectors and host cells are also included in the present invention and are known in the art.

The peptide of the present invention can be synthesized by peptide synthetic chemistry, for example the peptide of the invention can be synthesized by liquid-phase synthesis (*Combinatorial Chemistry: A Practical Approach*, ed. Hicham Fenniri, Oxford University Press (2000)) using standard procedure or by solid-phase synthesis, for example "Fmoc" or "Bmoc" synthesis, (*Fmoc Solid Phase Peptide Synthesis: A Practical Approach* (Practical Approach S.), ed.s W. Chan &, Peter White, Oxford University Press (2000)). When solid-phase synthesis is employed, then a solid phase is used, such as polystyrene resin or polyamide resin, or PEG hybrid polystyrene resin, or resin based on PEG. Different protective groups are used during the synthesis, for example, N-terminal protecting groups, t-Boc or FMOC protective groups. Moreover, benzyloxycarbonyl (Z) groups or allyloxycarbonyl (Alloc) protective groups, or photoremovable (lithographic) protective groups, or side group protection technique may be employed. Peptide products are purified by HPLC separation or by any other purification method. Peptide structure is confirmed by amino acid analysis, mass spectrometry, and high performance liquid chromatography data.

In some instances, fragments may be synthesised using solid-state methods and then coupled together in solution. Peptides can be synthesized from the carbonyl group side to amino group side of the amino acid chain in this method, although peptides are synthesized in the opposite direction in cells. In such methods, an amino-protected amino acid is bound to a substrate bead (i.e. a resin bead), forming a covalent bond between the carbonyl group and the resin. The amino group is then de-protected and reacted with the carbonyl group of the next amino-protected amino acid. The cycle is repeated as often as required in order to form the desired peptide chain. The synthesized peptide is then cleaved from the bead at the end of the procedure. The protecting groups for the amino groups mostly used in this peptide synthesis are 9-fluorenylmethyloxycarbonyl group ("Fmoc") and t-butyloxycarbonyl ("Boc"). The Fmoc group is removed from the amino terminus with base while the Boc group is removed with acid.

HEP-1 peptide, HP1-5 peptide, and HP6-14 peptide, used in the present invention for the preparation of the pharmaceutical compositions, were prepared by liquid-phase synthesis method by the licensed manufacturer "Immapharma", LLC (Moscow).

In a further aspect of the invention, there is provided a method of making the peptides of the invention, in particular peptides according to general formula 1, such as peptides comprising the amino acid sequence of SEQ ID No: 1 or SEQ ID No: 5. The method may comprise synthesizing the peptides by liquid-phase synthesis or solid-phase synthesis.

In one embodiment of the invention, there is provide a peptide of 14 amino acids in length, wherein the amino acid sequence is GEKKRRETVEREGG. The peptide is useful in medicine, in particular in treating lower gut inflammation and/or ulceration. The peptide may be provided in the form of a tablet for oral administration, in particular a glucose tablet.

Preferred features for the second and subsequent aspects of the invention are as for the first aspect mutatis mutandis.

The present invention will now be described by way of reference to the following Examples which are present for the purposes of reference only and are not to be construed as being limiting on the invention. In the Examples, reference is made to a number of drawings in which:

FIG. 1. High performance liquid chromatography of HEP-1 peptide. Luna C18 (2) column, 4.6×250 mm, 5.0 µm particles. Mobile phase: A—water, 5% ACN, 0.1% TFA; B—0.1% TFA; program 5-25% ACN for 20 min. Flow rate: 1 ml/min. X-axis: time, Y-axis: UV absorption (mV, upper line, with peaks), pressure (lower, horizontal line).

Figure 2:
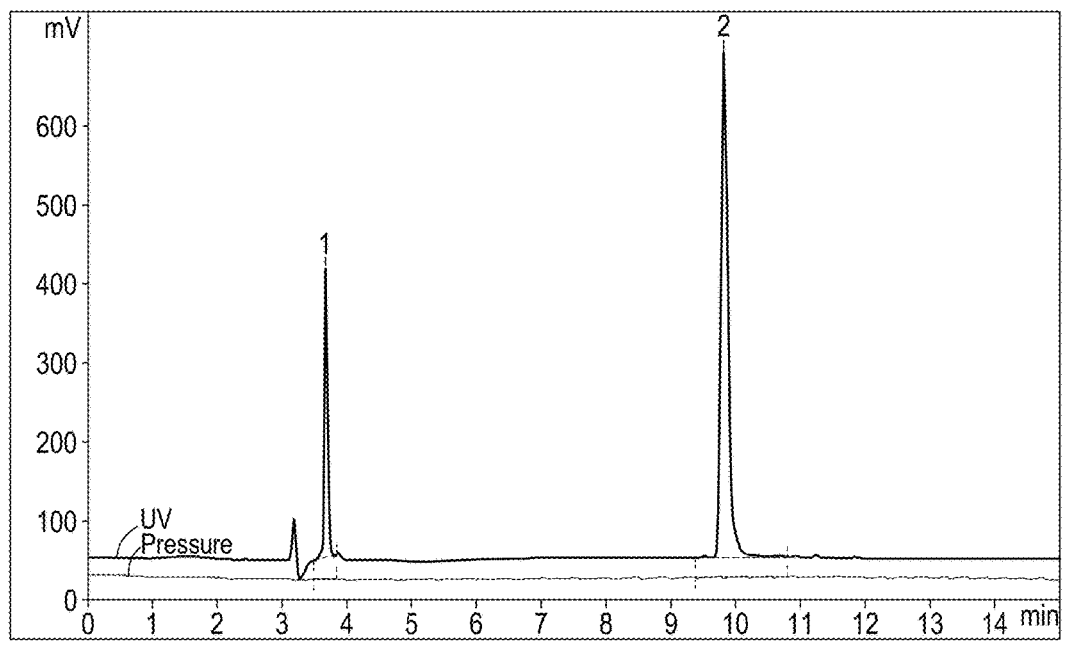

FIG. 2. High performance liquid chromatography of the mixture of HEP-1 peptide and HP 1-5 peptide. Luna C18 (2) column, 4.6×250 mm, 5.0 µm particles. Mobile phase: A—water, 5% ACN, 0.1% TFA; B—0.1% TFA; program 5-25% ACN for 20 min. Flow rate: 1 ml/min. X-axis: time, Y-axis: UV absorption (mV, upper line, with peaks), pressure (lower, horizontal line).

Figure 3:
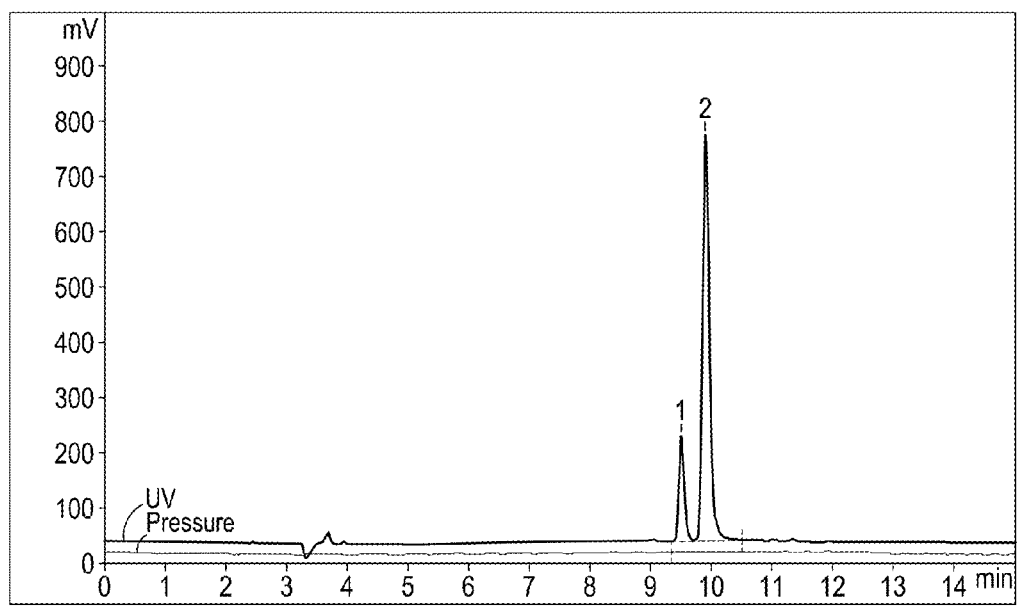

FIG. 3. High performance liquid chromatography of the mixture of HEP-1 peptide and HP 6-14 peptide. Luna C18 (2) column, 4.6×250 mm, 5.0 µm particles. Mobile phase: A—water, 5% ACN, 0.1% TFA; B—0.1% TFA; program 5-25% ACN for 20 min. Flow rate: 1 ml/min. X-axis: time, Y-axis: UV absorption (mV, upper line, with peaks), pressure (lower, horizontal line).

Figure 4:
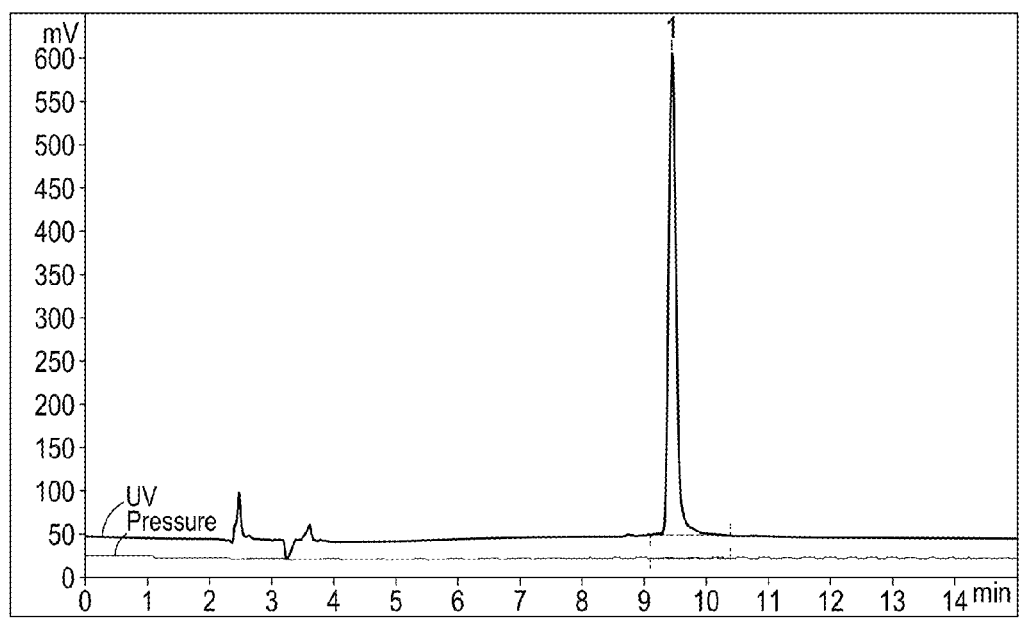

FIG. 4. High performance liquid chromatography of the mixture of HEP-1 peptide and HP-V2 peptide. Luna C18 (2) column, 4.6×250 mm, 5.0 µm particles. Mobile phase: A—water, 5% ACN, 0.1% TFA; B—0.1% TFA; program 5-25% ACN for 20 min. Flow rate: 1 ml/min. X-axis: time, Y-axis: UV absorption (mV, upper line, with peaks), pressure (lower, horizontal line).

Figure 5:
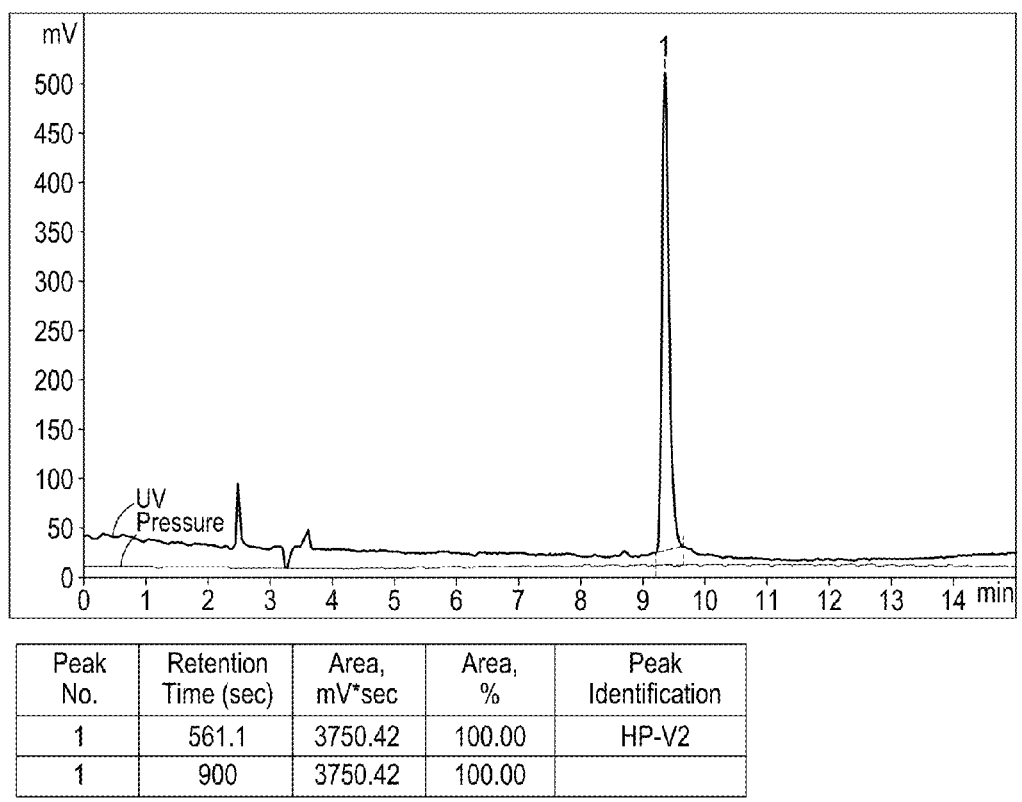

FIG. 5. High performance liquid chromatography of the mixture of HP-V2 peptide. Luna C18 (2) column, 4.6×250 mm, 5.0 pun particles. Mobile phase: A—water, 5% ACN, 0.1% TFA; B—0.1% TFA; program 5-25% ACN for 20 min. Flow rate: 1 ml/min. X-axis: time, Y-axis: UV absorption (mV, upper line, with peaks), pressure (lower, horizontal line).

Figure 6:
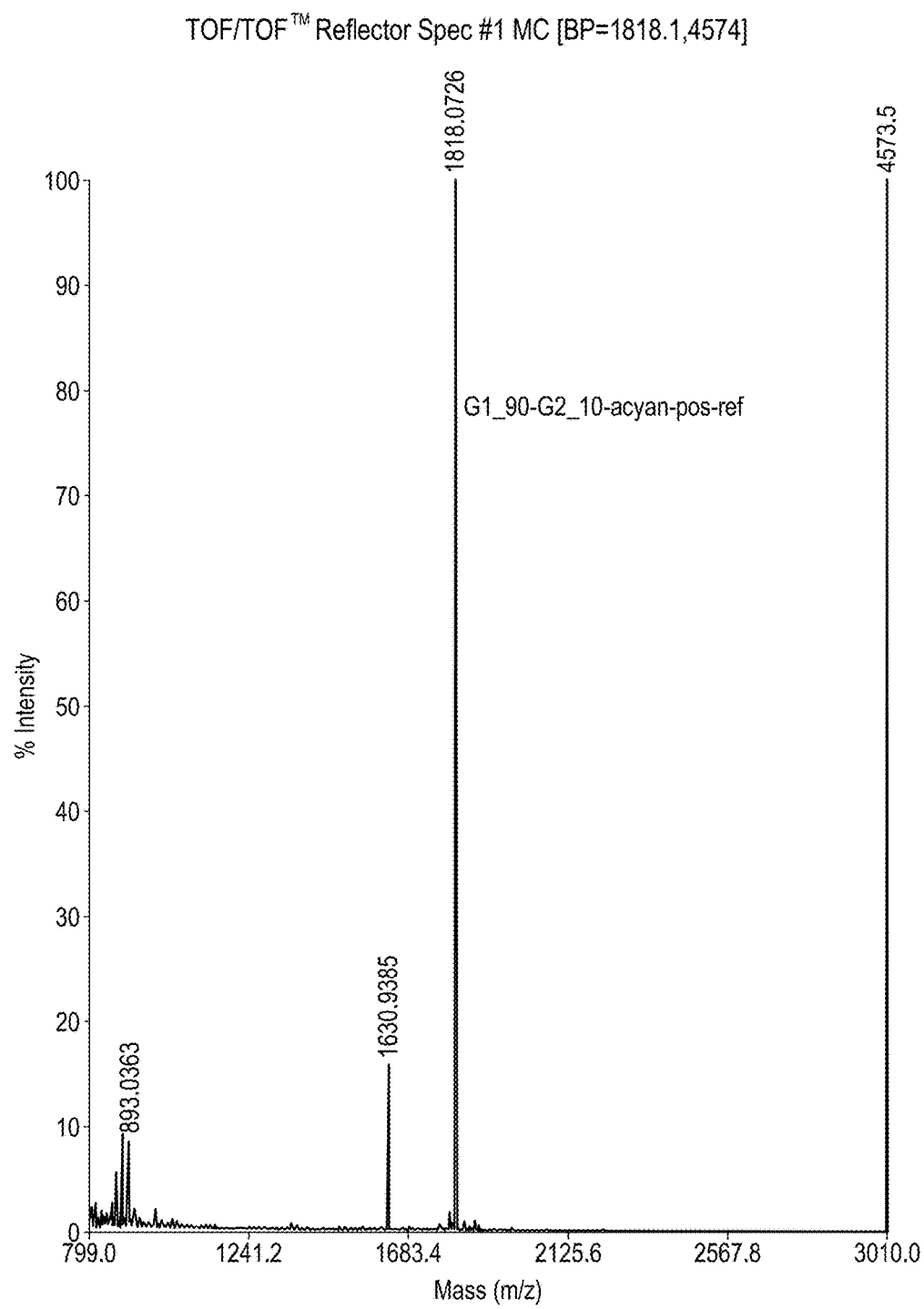

FIG. 6. MALDI TOF/TOF spectrum of the mixture of HEP-1 peptide and HP-V2 peptide.

EXAMPLES

The method of high performance liquid chromatography was used for accurate assessment of each component concentration during preparation of the pharmaceutical compositions. Results of the study demonstrated that it was impossible to distinguish HP-V2 peptide, having similar amino acid number with HEP-1 peptide, in the high performance liquid chromatography (HPLC) conditions, and this fact does not allow to access the quantitative content of the compositions based on HP-V2 and HEP-1 (Example 4; FIG. 1, FIG. 4, FIG. 5). Meanwhile the quantitative composition of the claimed HP-V2 peptide and satellite peptides HP1-5 and HP6-14 may be readily calculated based on the chromatograms as a consequence of their good separation (Examples 2, 3; FIG. 2, FIG. 3).

However MALDI TOF mass spectrometry clearly detects each peptide in the mixture of two peptides, comprising 14 amino acid residues, in particular, in the mixture of HP-V2 peptide (sequence ID No. 1: GEKKRRETVEREGG), which is defined as HP-V2, and HEP-1 peptide (sequence ID No. 2: TEKKRRETVEREKE), which is defined as HEP-1 (Example 5; FIG. 6).

Example 1. Preparation of HP-V2 Peptide

Synthesis of HP-V2 peptide was performed by solid-phase method using the alkoxybenzyl polymer. Couplings were performed employing the method based on the usage of either: 1) tetrafluoroborate O-(benzotriazol-1-yl)-N,N,N', N'-tetramethyluronium (TBTU); or 2) 1-hydroxybenzotriazole (HOBT) and N,N'-diisopropylcarbodiimide (DIPC). Attachment of the sequential Fmoc-protected amino acid residues was performed singly, except the cases when unreacted amino groups were found on the growing peptidyl-polymer after the coupling reaction. Control over the unreacted amino group content in the peptidyl-polymer was held by means of ninhydrin test. Trifluoroacetic acid with addition of thioanisole, phenol, ethanedithiol, triisopropylsilane, and water was used for separation of the peptide and polymeric carrier and for final unblocking. Structure and homogeneity of the desired product was confirmed by amino acid analysis, mass spectrometry, and high performance liquid chromatography data.

The following pharmaceutical compositions based on provided HP-V2 peptide (sequence ID No. 1: GEKKRRETVEREGG), as well as on the mixtures thereof with the following peptides were proposed:

HEP-1
(sequence ID No. 2: TEKKRRETVEREKE);

HP1-5
(sequence ID No. 3: TEKKR);

HP6-14
(sequence ID No. 4: RETVEREKE).

Pharmaceutical Compositions:

The pharmaceutical composition, comprising an effective amount of the peptide according to the sequence ID No. 1: GEKKRRETVEREGG, and a pharmaceutically acceptable carrier or filler—the others.

The pharmaceutical composition, comprising an effective amount of the peptide according to the sequence ID No. 1: GEKKRRETVEREGG, the peptide according to the sequence ID No. 2: TEKKRRETVEREKE, and a pharmaceutically acceptable carrier or filler—the others.

The pharmaceutical composition, comprising an effective amount of the peptide according to the sequence ID No. 1: GEKKRRETVEREGG, the peptide according to the sequence ID No. 3: TEKKR, and a pharmaceutically acceptable carrier or filler—the others.

The pharmaceutical composition, comprising an effective amount of the peptide according to the sequence ID No. 1: GEKKRRETVEREGG, the peptide according to the sequence ID No. 4: RETVEREKE, and a pharmaceutically acceptable carrier or filler.

The specific mixtures, comprising HP-V2 peptides and HEP-1, HP1-5, HP6-14, which were used for preparation of the pharmaceutical compositions, are provided in the Example 6.

HP-V2 peptide or mixtures thereof with abovementioned peptides in the amount of 0.01 mg to 1000 mg is dissolved in the volume of 1 ml to 10 ml of sterile water. Dosage forms may be prepared on the basis of prepared solution and may be used orally, anally, or vaginally, or intranasally as drops, or as spray for inhalation.

HP-V2 peptide or combination of peptides in the amount of 0.01 mg to 1000 mg is placed in a tablet or a capsule, or suppositories, or a gel, or an ointment formulation in combination with appropriate fillers, carriers, preservatives, and stabilizers, which are usually used by persons skilled in drug delivery technology.

HP-V2 peptide or combination of peptides in the abovementioned pharmaceutical compositions may be employed for the preparation of dosage forms, which may be used orally, anally, or vaginally, or which may be locally applied. Sterile solution, containing 0.01 mg to 1000 mg of HP-V2 peptide or combination of peptides, dissolved in the volume of 1 ml to 10 ml of water for injection or any physiologic saline, is administrated as injection by subcutaneous, intramuscular or intravenous route.

Example 2. Separation of HEP-1 and HP 1-5 Peptides by HPLC

High performance liquid chromatography (HPLC) was used for separation of the peptides based on the retention times thereof. Stock solutions of HEP-1 and HP 1-5 peptides were prepared by means of solubilization thereof in deionized water at a concentration of 1-2 mg/ml followed by filtration sterilization through Millipore filters with pore size 0.2 µm. Composition, containing 80% of HEP-1 peptide and 20% of HP 1-5 peptide, was prepared by mixing of the corresponding stock solutions in appropriate volumes.

HPLC was conducted on Luna C18 (2) column, 4.6×250 mm by size, filled with 5 µm particles. Mobile phase was prepared by program mixing of phases A and B, wherein A contained water, 5% acetonitrile (ACN), 0.1% TFA, and B contained 0.1% TFA. Programmed gradient 5 to 25% acetonitrile (ACN) was formed during 20 minutes. The sample volume was 20 µl; the flow rate was 1 ml/min. The peaks were recorded automatically by UV-absorption thereof at different retention times.

FIG. 1 illustrates HPLC peak of HEP-1 peptide with its typical retention time between 9 and 1-minutes. FIG. 2 illustrates the clear separation of two peaks, HEP-1 (RT=9.822 min) and HP1-5 (RT=3.666 min), by HPLC.

Example 3. Separation of HEP-1 and HP6-14 Peptides by HPLC

Stock solutions of HEP-1 and HP6-14 peptides and mixtures thereof were prepared as described in the Example 2. Analysis of the peptides and mixtures thereof by HPLC was conducted on Luna C18 (2) column, 4.6×250 mm by size, filled with 5 µm particles as described in the Example 1.

In HPLC conditions used, the mixture of HEP-1 and HP6-14 peptides was clearly separated into 2 peaks (FIG. 3), one of which had the retention time, which was typical for HP6-14 peptide (RT-9.495 min), and the other one had the retention time, which was typical for HEP-1 peptide (RT=9.894 min).

Example 4. Analysis of the Mixture of HEP-1 and HP-V2 Peptides by HPLC

Stock solutions of HEP-1 and HP-V2 peptides, as well as mixtures thereof were prepared as described in the Example 2. HPLC analysis of the peptides and the mixtures was conducted on Luna C18 (2) column, 4.6×250 mm by size, filled with 5 µm particles as described in the Example 2.

In HPLC conditions used, the mixture of HEP-1 and HP-V2 peptides was eluted from the column as one peak (FIG. 4) with the retention time, which was typical for HEP-1 peptide. HPLC-analysis of HP-V2 peptide solution alone has shown (FIG. 5) that the retention time of this peptide, indeed, was the same as the retention time of HEP-1 peptide. It means that it is impossible to distinguish HP-V2 and HEP-1 peptides in this HPLC conditions.

Example 5. The Mass Spectrometry of the Mixture of HEP-1 and HP-V2 Peptides

Stock solutions of HEP-1 and HP-V2 peptides, as well as mixtures thereof, were prepared as described in the Example 2. MALDI TOF spectra were reordered on the Bruker Ultraflex TOF/TOF mass spectrometer using 2,5-dihydroxybenzoic acid as a matrix.

The mass spectrum of the mixture of HEP-1 and HP-V2 peptides (FIG. 6) clearly reveals both peptides with their molecular ions 1818.0726 (MW) for HEP-1 and 1630.9385 (MW) for HP-V2.

Introduction to Examples 6-8

The following Examples 6-8 demonstrate biological activity of all the peptides used and mixtures thereof. These peptides induce interferon production and protect different types of human cells from death caused by infection of cytopathic encephalomyocarditis virus at a dose of 100 TCID50/ml in the cell cultures in vitro.

Peptide (HP-V2) (sequence ID No. 1: GEKKRRET-VEREGG), comprising 14 amino acid residues, and compositions thereof with HEP-1 peptide (sequence ID No. 2: TEKKRRETVEREKE), or with HP1-5 peptide (sequence ID No. 3: TEKKR), or with HP6-14 peptide (sequence ID No. 4: RETVEREKE) were studied for their ability to induce antiviral response with production of the I type interferon in the cultures of different cells. We used the conventional methodology of antiviral (interferon-inducing) activity testing of the compounds in the culture in vitro, which is widely used for screening of immunostimulatory, antiviral drugs, and interferon inducers.

In this methodology in vitro, we pretreated different types of cells with the studied peptides, and then the cells were infected with a dose of 100 LD50 of encephalomyocarditis virus. 24 hours after the infection the cytopathic effect of the virus was assessed in order to evaluate protective activity of the tested compound if the latter has the ability to bring the cells to a state, resistant to the virus, which is deadly for cells.

As it is well known, in the vast majority of cases such protective activity of the compounds is predicated upon interferons induction (the term <<interferon>> means the compound, which is produced by cell and which prevents replication of the virus). It was possible to evaluate antiviral (interferon-inducing) activity of these compounds by using of different concentrations of said peptides and compositions thereof in vitro.

The lower is the concentration which protects 50% of cells from death due to the infection at a dose of 100 LD50 of encephalomyocarditis virus, the higher is antiviral (interferon-inducing) activity of the tested compound.

Peptide (HP-V2) (sequence ID No. 1: GEKKRRET-VEREGG), comprising 14 amino acid residues, and combinations thereof with HEP-1 peptide (sequence ID No. 2: TEKKRRETVEREKE), or with HP1-5 peptide (sequence ID No. 3: TEKKR), or with HP6-14 peptide (sequence ID No. 4: RETVEREKE) were tested with respect to the immunostimulatory (antiviral, interferon-inducing) activity.

Example 6. Study of Antiviral (Interferon-Inducing) Activity of the Peptides in the Culture of Human Hepatoma Cell Line PLC/PRF/5 (Alexander) human hepatoma cell line was obtained from Research Institute of Virology named after Ivanovskiy (Moscow). Complete medium for cells culturing was prepared on the basis of MEM Eagle medium supplemented with 10% fetal calf serum (FCS), L-glutamine (300 μg/ml), and penicillin (100 U/ml).

The following peptides were tested:

```
HEP-1
(sequence ID No. 2: TEKKRRETVEREKE);

HP1-5
(sequence ID No. 3: TEKKR);

HP6-14
(sequence ID No. 4: RETVEREKE);

HP-V2
(sequence ID No. 1: GEKKRRETVEREGG);
```

Mixtures of Peptides:
MXHP1-5+HEP-1—the mixture of 90% HEP-1 peptide (sequence ID No. 2: TEKKRRETVEREKE) and 10% of HP1-5 peptide (sequence ID No. 3: TEKKR);

MXHP6-14+HEP-1—the mixture of 90% HEP-1 peptide (sequence ID No. 2: TEKKRRETVEREKE) and 10% of HP6-14 peptide (sequence ID No. 4: RETVEREKE);

MXHP-V2+HP1-5—the mixture of 90% HP-V2 peptide (sequence ID No. 1: GEKKRRETVEREGG) and 10% of HP1-5 peptide (sequence ID No. 3: TEKKR);

MXHP-V2+HP6-14—the mixture of 90% HP-V2 peptide (sequence ID No. 1: GEKKRRETVEREGG) and 10% of HP6-14 peptide (sequence ID No. 4: RETVEREKE).

MXHP-V2+HEP-1—the mixture of 95% HP-V2 peptide (sequence ID No. 1: GEKKRRETVEREGG) and 5% of HEP-1 peptide (sequence ID No. 2: TEKKRRETVEREKE).

The peptides were dissolved in distilled water, and then sterilized by passing through filters with pore size 0.2 μm to obtain the stock solutions of 1-2 mg/ml. On day 0, cells were seeded in the wells of 96-well plate in complete culture medium with cell density of 200 thousands of cells in 1 ml. On day 1, serial dilutions of each tested sample were prepared (24 serial dilutions in increments of 2) in triplets in the wells of the 96-well plate. On day 3, all the cultures were infected with a dose of 100 $TCID_{50}$/ml of encephalomyocarditis virus strain "Columbia SK-Col-SK". Finally, on day 4, cytopathic effect of the virus was assessed by using Leitz inverted microscope in the presence of different concentrations of the tested peptide or in the cultures without peptide (control).

Antiviral effect of the drug product was assessed based on minimal concentration thereof protecting 50% of the cells from death caused by encephalomyocarditis virus at a dose of 100 $TCID_{50}$/ml. Interferon titre (U/ml) was calculated as a value, inverse to the maximal dilution of the drug product, which protected 50% of the cells from death caused by encephalomyocarditis virus at a dose of 100 $TCID_{50}$/ml.

The data obtained are presented in the Table 1. It is evident that all the tested peptides and combinations thereof prevent the replication of encephalomyocarditis virus in human hepatoma cells. The peptides have protected hepatoma cells from cytopathic effect of the virus by inducing interferon production. Efficacy of the peptides and compositions thereof was different. The highest level of antiviral (interferon-inducing) activity was registered with HP-V2 peptide and its composition with HP1-5 peptide.

TABLE 1

Antiviral (interferon-inducing) activity of the peptides in the culture of PLC/PRF/5 (Alexander) human hepatoma cell line.

| Compound | The maximal concentration tested (μg/ml) | Antiviral efficacy (μg/ml) † | Titre of induced interferon (U/ml) ‡ |
|---|---|---|---|
| HEP-1 | 100 | 3.0 | 320 |
| HP1-5 | 100 | 1.6 | 640 |
| HP6-14 | 100 | 0.78 | 1280 |
| MXHP1-5 + HEP-1 | 200 | 62.5 | 16 |
| MXHP6-14 + HEP-1 | 200 | 62.5 | 16 |
| MXHP-V2 + HP1-5 | 100 | 0.1 | 10240 |
| MXHP-V2 + HP6-14 | 100 | 3.0 | 320 |
| MXHP-V2 + HEP1 | 100 | 0.78 | 1280 |
| HP-V2 | 100 | 0.78 | 1280 |

Notes:
† The antiviral efficacy is shown as the minimal compound concentration, protecting 50% of the cells from death as a result of infecting of 100 LD50 of encephalomyocarditis virus
‡ The titre of induced interferon was calculated as a value, inverse to the maximal dilution of the compound, which protected 50% of the cells from death as a result of infecting of 100 LD50 of encephalomyocarditis virus.

Example 7. Study of Antiviral (Interferon-Inducing) Activity of the Peptides in the Culture of Human Cervical Carcinoma Cell Line HELA human cervical carcinoma cell line was obtained from Research Institute of Virology named after Ivanovskiy (Moscow). Complete medium for cells culturing, peptides and compositions thereof, as well as assessment method for their antiviral (interferon-inducing) activity were the same as described in the Example 5.

The data obtained are presented in the Table 2. It is evident that all the tested peptides and the compositions prevent the development of encephalomyocarditis virus infection in the human cervical carcinoma cells. The peptides have protected cervical carcinoma cells from cytopathic effect of the virus by inducing interferon production. The peptides and compositions thereof had different activity. The maximal antiviral (interferon-inducing) activity was detected when using HP1-5 peptide (sequence ID No. 3: TEKKR) and HP 6-14 peptide (sequence ID No. 4: RETVEREKE), as well as combinations thereof with HP-V2 peptide.

TABLE 2

Antiviral (interferon-inducing) activity of the peptides in the culture of HELA human cervical carcinoma cell line.

| Compound | The maximal concentration tested (µg/ml) | Antiviral efficacy (µg/ml) † | Titre of induced interferon (U/ml) ‡ |
|---|---|---|---|
| HEP-1 | 1000 | 3.9 | 256 |
| HP1-5 | 1000 | 0.49 | 2048 |
| HP6-14 | 1000 | 0.49 | 2048 |
| MXHP1-5 + HEP-1 | 2000 | 7.8 | 256 |
| MXHP6-14 + HEP-1 | 2000 | 1.95 | 1024 |
| MXHP-V2 + HP1-5 | 1000 | 0.97 | 1024 |
| MXHP-V2 + HP6-14 | 1000 | 0.49 | 2048 |
| HP-V2 | 1000 | 7.8 | 128 |

Notes:
† The antiviral efficacy is shown as the minimal compound concentration, protecting 50% of the cells from death as a result of infecting of 100 LD50 of encephalomyocarditis virus.
‡ The titre of induced interferon was calculated as a value, inverse to the maximal dilution of the compound, which protected 50% of the cells from death as a result of infecting of 100 LD50 of encephalomyocarditis virus.

Example 8. Study of Antiviral (Interferon-Inducing) Activity of the Peptides in the Culture of Girardi Heart Human Epithelial Cell Line The culture of Girardi Heart human epithelial cell line was obtained from Research Institute of Virology named after Ivanovskiy (Moscow). Complete medium for cells culturing, peptides and compositions thereof, as well as assessment method for their antiviral (interferon-inducing) activity were the same as described in the Example 5.

The results obtained are presented in the Table 3. It is evident from the presented data that all the tested peptides and compositions prevent the development of encephalomyocarditis virus infection in the cells of Girardi Heart human epithelial cell line. The tested peptides and compositions thereof were highly effective in the inducing of interferons production and in the protection of Girardi Heart epithelial cell line from cytopathic effect of the virus. The maximal antiviral (interferon-inducing) activity was detected when using of HEP-1 peptide (sequence ID No. 2: TEKKRRETVEREKE) with HP1-5 peptide (sequence ID No. 3: TEKKR) and HP6-14 peptide (sequence ID No. 4: RETVEREKE) combinations, as well as the combination of HP-V2 peptide (sequence ID No. 1: GEKKRRETVEREGG) with HP1-5 peptide (sequence ID No. 3: TEKKR) and with HEP1 peptide (sequence ID No. 2: TEKKRRETVEREKE).

TABLE 3

Antiviral (interferon-inducing) activity of the peptides in the culture of Girardi Heart epithelial cell line

| Compound | The maximal concentration tested (µg/ml) | Antiviral efficacy (µg/ml) † | Titre of induced interferon (U/ml) ‡ |
|---|---|---|---|
| HEP-1 | 1000 | 0.0015 | 655 360 |
| HP1-5 | 1000 | 0.0015 | 655 360 |
| HP6-14 | 1000 | 0.006 | 163 840 |
| MXHP1-5 + HEP-1 | 2000 | 0.0005 | 4 194 304 |
| MXHP6-14 + HEP-1 | 2000 | 0.0005 | 4 194 304 |
| MXHP-V2 + HP1-5 | 1000 | 0.0002 | 5 242 880 |
| MXHP-V2 + HP6-14 | 1000 | 0.006 | 163 840 |
| MXHP-V2 + HEP1 | 1000 | 0.0008 | 1 310 720 |
| HP-V2 | 1000 | 0.0015 | 655 360 |

Notes:
† The antiviral efficacy is shown as the minimal compound concentration, protecting 50% of the cells from death as a result of infecting of 100 LD50 of encephalomyocarditis virus
‡ The titre of induced interferon was calculated as a value, inverse to the maximal dilution of the compound, which protected 50% of the cells from death as a result of infecting of 100 LD50 of encephalomyocarditis virus As the provided examples with description of biological tests and the tables demonstrate, the proposed novel HP-V2 peptide possesses high immunostimulatory activity, which is the same (Table 3) or which is 4 times higher (Table 1) when comparing with the activity of known HEP-1 peptide. Moreover, the pharmaceutical compositions with the highest immunostimulatory activity and with a wide range of action (Tables 1-3), which are in several times higher than those known for HEP-1 peptide and compositions thereof, were obtained based on the claimed HP-V2 peptide and known Ezrin peptides.

Example 9. Study to Show Influence of Peptide on Molecular Mechanism in Tissue Repair and Cell Proliferation The following study provides evidence that the peptide of the invention (HP-V2) is involved in the molecular mechanism of tissue repair and cell proliferation. It is known that compounds which influence the molecular mechanism of cell proliferation, for example regulation of the TGFβ expression is associated with repair of the gut (Monteleone et al., "Mongersen, an Oral SMAD7 Antisense Oligonucleotide, and Crohn's Disease", *New England Journal of Medicine*, 372:1104-1113). In addition, Akita et al., "Basic Fibroblast Growth Factor in Scarless Wound Healing", *Adv. Wound Care*, 2013, 2(2):44-49 discusses the benefit and role of basic fibroblast growth factor (bFGF) in scarless wound healing in clinical application and basic mechanism. bFGF is a glycoprotein which is widely used in treating wounds and ulcers. bFGF is easily applicable to any type of wound and leads to a better outcome in color, texture, and firmness. Chen et al., "NGF Accelerates Cutaneous Wound Healing by Promoting the Migration of Dermal Fibroblasts via the PI3K/Akt-Rac1-JNK and ERK Pathways", *BioMed Research International*, Volume 2014, Article ID 547187) showed that NGF significantly accelerated the healing of skin excisional wounds in rats and the fibroblast migration induced by NGF may contribute to this healing process. This also showed that the activation of PI3K/Akt, Rac1, JNK, and ERK were all involved in the regulation of NGF-induced fibroblast migration. Further, Raffetto et al., "Mitogen-activated protein kinase pathway regulates cell proliferation in venous ulcer fibroblasts", *Vasc. Endovascular Surg.*, 2006, 40(1):59-66 showed that MAPK ERK pathway is important for cell proliferation in venous ulcer fibroblasts.

Hence, the peptides of the invention are useful in the prevention and treatment of lower gut inflammation and ulceration.

It is shown that peptide GEKKRRETVEREGG (SEQ ID No: 1) induces activation of fibroblasts which are the main cell type responsible for tissue regeneration, as well as healing of wounds and ulcers. This example demonstrates direct activating influence of peptide GEKKRRETVEREGG (SEQ ID No: 1) on mouse fibroblasts, revealing quick activation signature within the cells on the level of MAPK-ERK signaling pathway.

Peptide GEKKRRETVEREGG (SEQ ID No: 1) was obtained as described in Example 1, BALB/c mouse fibroblast were purchased from American Type Culture Collection and propagated in a complete medium consisting of high glucose DMEM supplemented with 10% fetal calf serum, 1 mM sodium pyruvate, 1:50 MEM non-essential amino acids, 2 mM L-glutamine, 10 µg/ml gentamicin and 50 µM β-mercaptoethanol. Cells were grown in 10 cm culture dishes at 5% CO2 and 37° C. Cell passages were made at the 50-60% confluency. For cell detachment, 0.05% trypsin/EDTA was used with following centrifugation (470× g, 15 min) in 10-fold volume of washing medium containing 10% FCS to quench trypsin. Supernatant was discarded and the cell pellet was suspended in 10 ml of complete culture medium, then cell numbers were counted using hemocytometer before cells were used for experiments.

Fibroblasts were cultured in 8-well culture plates, the examined peptide or cytokine TGF-β1 (positive control) solution, or equivalent volume of culture medium (negative control) were added into respective triplicate cultures. Cells were incubated in presence of the peptide GEKKRRETVEREGG SEQ ID No: 1 (10 µg/ml) or TGF-β1, or without any effector compound during 1 or 6 hours at 5% C02 and 37° C. At the time points indicated, cell were harvested, washed twice with PBS and lyzed using the cell extraction buffer in the presence of protease inhibitors during 30 min at 4° C. Extracts were cleared by centrifugation (14,000×g, 10 min, 4° C.). Protein concentration was measured using protein assay reagent (Pierce, 23225). Appropriate dilutions of extracts (10 g protein per a track) were then fractionated in 8% SDS-PAGE and then transferred onto PVDF-membrane (Amersham) for immune blotting. Targeted proteins were detected using antibodies specific to phospho-p44/42 MAPK (Cell Signaling, 4370) and GAPDH (Abcam ab8245). Protein bands were visualized and then measured their intensities using ImageJ soft-ware. Data were expressed as a value (pixels per a band) of ERK1, ERK2 or phospho-ERK1 and phospho-ERK2 normalized to a value of respective GAPDH-bands. Mean values+SD were calculated using the data of 3 independent runs.

Results of our experiments show that both the peptide GEKKRRETVEREGG (SEQ ID No: 1) and the positive control TGF-β1 induce a rapid activation of MAPK/ERK signaling pathway in fibroblasts. In 1 hour after inoculation of these effector compounds a concentration of phosphorylated ERK1 (44 kD) and ERK2 (42 kD) was increased approximately 3-5-fold. Thus, 1 hour. after activation of fibroblasts with the GEKKRRETVEREGG (SEQ ID No: 1) peptide (10 µg/ml) or TGF-β1 (5 ng/ml), pospho-ERK1 normalized values were 0.4+0.02 (p<0.01) and 0.5+0.02 (p<0.01), respectively, as compared to 0.1+0.002 in the negative control, and phospho-ERK2 values were 1.3+0.05 (p<0.01) and 1.9+0.1 (p<0.01) as compared to 0.4+0.01 in the negative control. Later, 6 hours after activation, the values of pospho-ERK1 in fibroblasts activated with the peptide GEKKRRETVEREGG (SEQ ID No: 1) or TGF-β1 were 0.1+0.006 (p>0.1) and 0.3+0.02 (p<0.05), respectively, while 0.1+0.01 in the negative control cultures. Pospho-ERK2 values at the 6 hour time point were 0.1+0.01 (p>0.1), 0.35+0.02 (p<0.01) and 0.1+0.007 in the peptide, TGF-β1 and non-activated cultures, respectively.

The above study has shown that the activity of HP-V2 resembles the activity of TGF β (the positive control), and thus the potential for use in the prevention and treatment of lower gut inflammation and ulceration.

---

The invention claimed is:

1. A peptide comprising an amino acid sequence of general formula (I)

X1EKKRRETVEREX2X3 (SEQ ID No:5)

wherein each of X1, X2 and X3 represent a non-polar amino acid residue.

2. The peptide as claimed in claim 1, wherein the non-polar amino acid is independently selected from the group consisting of glycine, alanine, valine, leucine, methionine, isoleucine, proline, phenylalanine, tryptophan, and/or combinations thereof.

3. The peptide as claimed in claim 1, wherein X1 X2 and/or X3 is glycine.

4. The peptide as claimed in claim 3, wherein the amino acid sequence is GEKKRRETVEREGG (SEQ ID No: 1).

5. A pharmaceutical composition, comprising an effective amount of the peptide as claimed in claim 1, and a pharmaceutically acceptable carrier or filler.

6. The pharmaceutical composition as claimed in claim 5, further comprising an effective amount of the peptide according to SEQ ID No. 2 (TEKKRRETVEREKE).

7. The pharmaceutical composition as claimed in claim 5, further comprising an effective amount of the peptide according to the SEQ ID No.3 (TEKKR).

8. The pharmaceutical composition as claimed in claim 5, further comprising an effective amount of the peptide according to the SEQ ID No. 4 (RETVEREKE).

9. A method of stimulating an immune response in a subject in need thereof, comprising administering to the subject a therapeutically effective amount of the peptide as claimed in claim 1.

10. A method of stimulating an immune response in a subject in need thereof, comprising administering to the subject a therapeutically effective amount of the pharmaceutical composition as claimed in claim 5.

* * * * *

SEQUENCE LISTING

<160> NUMBER OF SEQ ID NOS: 6

<210> SEQ ID NO 1
<211> LENGTH: 14
<212> TYPE: PRT
<213> ORGANISM: Artificial Sequence
<220> FEATURE:
<223> OTHER INFORMATION: Synthetic peptide - HP-V2 peptide

<400> SEQUENCE: 1

Gly Glu Lys Lys Arg Arg Glu Thr Val Glu Arg Glu Gly Gly
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Fragment of human ezrin protein - HEP-1

<400> SEQUENCE: 2

Thr Glu Lys Lys Arg Arg Glu Thr Val Glu Arg Glu Lys Glu
1               5                   10

```
<210> SEQ ID NO 3
<211> LENGTH: 5
<212> TYPE: PRT
<213> ORGANISM: Artificial Sequence
<220> FEATURE:
<223> OTHER INFORMATION: Satellite peptide of human ezrin protein -
      HP1-5

<400> SEQUENCE: 3

Thr Glu Lys Lys Arg
1               5

<210> SEQ ID NO 4
<211> LENGTH: 9
<212> TYPE: PRT
<213> ORGANISM: Artificial Sequence
<220> FEATURE:
<223> OTHER INFORMATION: Satellite peptide of human ezrin protein -
      HP6-14

<400> SEQUENCE: 4

Arg Glu Thr Val Glu Arg Glu Lys Glu
1               5

<210> SEQ ID NO 5
<211> LENGTH: 14
<212> TYPE: PRT
<213> ORGANISM: Artificial Sequence
<220> FEATURE:
<223> OTHER INFORMATION: synthetic fragment of human ezrin protein -
      general formula I
<220> FEATURE:
<221> NAME/KEY: Variant
<222> LOCATION: (1)..(1)
<223> OTHER INFORMATION: /replace="Gly" /replace="Ala" /replace="Val"
      /replace="Leu" /replace="Met" /replace="Ile" /replace="Pro"
      /replace="Phe" /replace="Trp"
<220> FEATURE:
<221> NAME/KEY: Variant
<222> LOCATION: (13)..(13)
<223> OTHER INFORMATION: /replace="Gly" /replace="Ala" /replace="Val"
      /replace="Leu" /replace="Met" /replace="Ile" /replace="Pro"
      /replace="Phe" /replace="Trp"
<220> FEATURE:
<221> NAME/KEY: Variant
<222> LOCATION: (14)..(14)
<223> OTHER INFORMATION: /replace="Gly" /replace="Ala" /replace="Val"
      /replace="Leu" /replace="Met" /replace="Ile" /replace="Pro"
      /replace="Phe" /replace="Trp"

<400> SEQUENCE: 5

Xaa Glu Lys Lys Arg Arg Glu Thr Val Glu Arg Glu Xaa Xaa
1               5                   10

<210> SEQ ID NO 6
<211> LENGTH: 11
<212> TYPE: PRT
<213> ORGANISM: Artificial Sequence
<220> FEATURE:
<223> OTHER INFORMATION: fragment of human ezrin protein - HEP-1
      residues 2-12

<400> SEQUENCE: 6

Glu Lys Lys Arg Arg Glu Thr Val Glu Arg Glu
1               5                   10
```